United States Patent
Kwon et al.

(10) Patent No.: US 10,743,820 B2
(45) Date of Patent: Aug. 18, 2020

(54) METHOD AND APPARATUS FOR MEASURING BIOSIGNAL

(71) Applicant: Samsung Electronics Co., Ltd., Suwon-si (KR)

(72) Inventors: Ui Kun Kwon, Hwaseong-si (KR); Sang Joon Kim, Hwaseong-si (KR); Jong Wook Lee, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 360 days.

(21) Appl. No.: 15/843,767

(22) Filed: Dec. 15, 2017

(65) Prior Publication Data

US 2018/0103910 A1 Apr. 19, 2018

Related U.S. Application Data

(62) Division of application No. 14/642,963, filed on Mar. 10, 2015, now Pat. No. 9,877,685.

(30) Foreign Application Priority Data

Sep. 1, 2014 (KR) .................. 10-2014-0115512

(51) Int. Cl.
*A61B 5/00* (2006.01)
*A61B 5/053* (2006.01)

(52) U.S. Cl.
CPC .......... *A61B 5/7221* (2013.01); *A61B 5/0533* (2013.01); *A61B 5/4035* (2013.01); *A61B 5/4266* (2013.01); *A61B 5/6843* (2013.01)

(58) Field of Classification Search
CPC ... A61B 5/0531; A61B 5/0533; A61B 5/4035; A61B 5/4266; A61B 5/6843; A61B 5/7221

See application file for complete search history.

(56) References Cited

U.S. PATENT DOCUMENTS

| | | | |
|---|---|---|---|
| 6,807,444 B2 | 10/2004 | Tu et al. | |
| 8,137,270 B2 | 3/2012 | Keenan et al. | |
| 9,002,444 B2 | 4/2015 | Jang et al. | |
| 9,295,403 B1 | 3/2016 | Mirov et al. | |
| 9,380,949 B2 | 7/2016 | Schuessler | |
| 9,427,158 B2 | 8/2016 | Choi et al. | |
| 9,579,457 B2 * | 2/2017 | Osorio | A61M 5/1723 |

FOREIGN PATENT DOCUMENTS

| | | |
|---|---|---|
| EP | 2-158-838 A1 | 3/2010 |
| JP | 09-271466 A | 10/1997 |
| JP | 2002-085364 A | 3/2002 |
| JP | 2003-111106 A | 4/2003 |
| JP | 2004-305686 A | 11/2004 |
| KR | 10-0817272 B1 | 3/2008 |
| KR | 10-2009-0029561 A | 3/2009 |
| KR | 10-2012-0007558 A | 1/2012 |
| KR | 10-1324560 B1 | 11/2013 |

* cited by examiner

*Primary Examiner* — Max F Hindenburg
(74) *Attorney, Agent, or Firm* — NSIP Law

(57) ABSTRACT

A biosignal measuring method and apparatus are provided. The biosignal measuring method includes verifying whether a measured biosignal is in a range, and controlling an operation of the biosignal measuring apparatus when the measured biosignal deviates from the range based on a result of the verifying.

7 Claims, 8 Drawing Sheets

METHOD AND APPARATUS FOR MEASURING BIOSIGNAL

CROSS-REFERENCE TO RELATED APPLICATION

This application is a Divisional of U.S. application Ser. No. 14/642,963, filed on Mar. 10, 2015, which claims the benefit under 35 USC 119(a) of Korean Patent Application No. 10-2014-0115512, filed on Sep. 1, 2014, in the Korean Intellectual Property Office, the entire disclosure of which is incorporated herein by reference for all purposes.

BACKGROUND

1. Field

The following description relates to an apparatus and a method for measuring a biosignal.

2. Description of Related Art

Human being emotions may be measured or recognized by a device using face or voice recognition. In addition to the recognition, research has been conducted on a method of extracting an emotion based on a biosignal. For example, an emotion may be measured based on an electrical conductance of skin. A general application of such electrical conductance may include a lie detector and a concentration measurer.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided a biosignal measuring method, the method including measuring a biosignal of a user of a biosignal measuring apparatus, verifying whether the biosignal is in a reference range, generating a biosignal adjustment event based on a result of the verification, and adjusting a setting of the biosignal measuring apparatus in response to the biosignal adjustment event.

When the biosignal deviates from the reference range, the adjusting of the setting may include controlling at least one of a temperature of a contact area between the user of the biosignal measuring apparatus and a change in grip between the user of the biosignal measuring apparatus and the biosignal measuring apparatus.

When the biosignal is in a range less than the reference range, the adjusting of the setting may include performing at least one of an operation of generating heat in a measurement area in which the biosignal is measured and an operation of tightening the biosignal measuring apparatus to the user.

In another general aspect, there is provided a biosignal measuring method, the method including measuring a biosignal of a user of a biosignal measuring apparatus, generating a biosignal adjustment event based on whether the biosignal is in a threshold range, adjusting a setting of the biosignal measuring apparatus in response to the biosignal adjustment event, and detecting whether the biosignal reaches a measurement range based on the adjusting.

When the biosignal is less than a first boundary value of the threshold range, the adjusting may include performing at least one of an operation of generating heat in a measurement area in which the biosignal is measured and an operation of tightening the biosignal measuring apparatus to the user of the biosignal measuring apparatus.

When the biosignal is greater than a second boundary value of the threshold range, the adjusting of the setting may include performing at least one of an operation of cooling the measurement area in which the biosignal is measured and an operation of releasing a grip between the biosignal measuring apparatus and the user of the biosignal measuring apparatus.

In still another general aspect, there is provided a biosignal measuring apparatus including a measurer configured to measure a biosignal of a user of the biosignal measuring apparatus, and a controller configured to verify whether the biosignal is in a reference range, generate a biosignal adjustment event based on a result of the verifying, and adjust a setting of the biosignal measuring apparatus in response to the biosignal adjustment event.

When the biosignal is in a range greater than the reference range, the controller may control the biosignal measuring apparatus to perform at least one of an operation of cooling the measurer and an operation of releasing a grip between the biosignal measuring apparatus and the user of the biosignal measuring apparatus.

The biosignal may be an electrical conductance of skin.

Other features and aspects will be apparent from the following detailed description, the drawings, and the claims.

Figure 1:
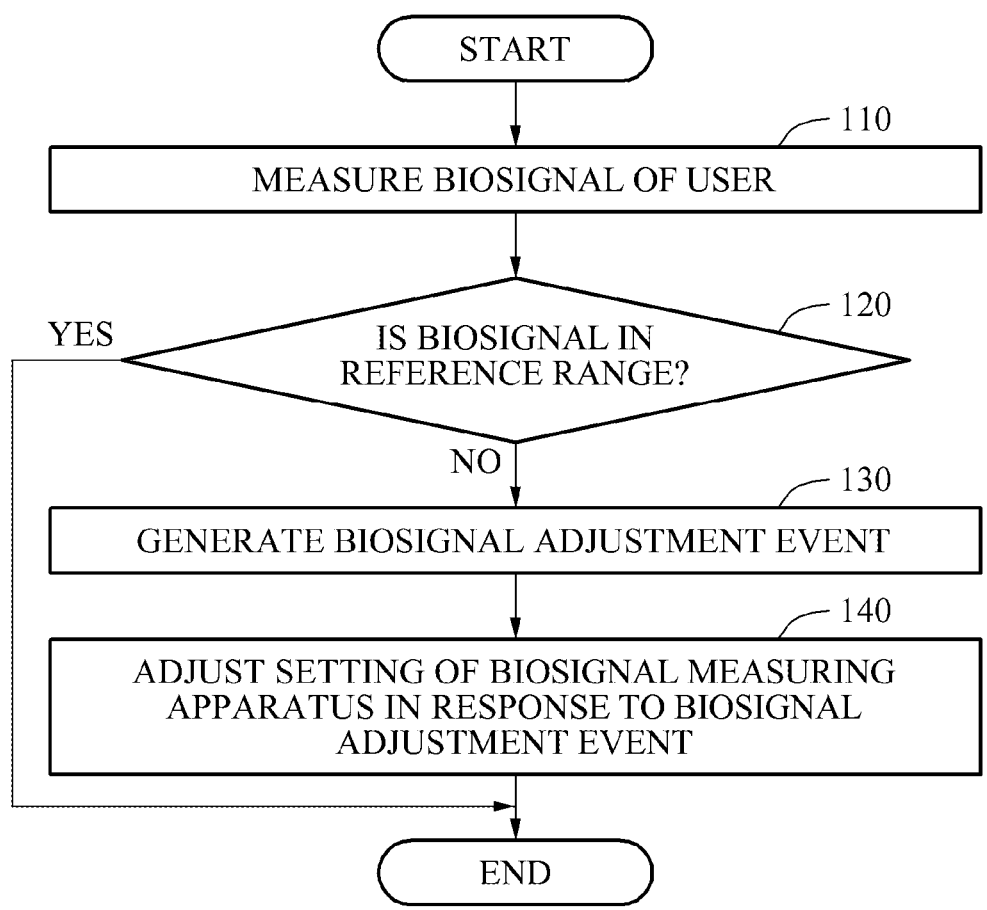
FIG. 1 is a flowchart illustrating an example of a biosignal measuring method.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses and/or methods described herein will be apparent to one of ordinary skill in the art. Also, descriptions of functions and constructions that are well known to one of ordinary skill in the art may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Example embodiments will now be described more fully with reference to the accompanying drawings in which example embodiments are shown. Example embodiments, may, however, be embodied in many different forms and should not be construed as being limited to the embodiments set forth herein; rather, these example embodiments are provided so that this disclosure will be thorough and complete, and will fully convey the scope of example embodiments to those of ordinary skill in the art. In the drawings, the thicknesses of layers and areas are exaggerated for clarity. Like reference numerals in the drawings denote like elements, and thus their description may be omitted.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a flowchart illustrating an example of a biosignal measuring method. The biosignal measuring method to be described hereinafter with reference to FIG. 1 may be performed by a biosignal measuring apparatus.

Referring to FIG. 1, at operation 110, the biosignal measuring apparatus measures a biosignal of a user. For example, the biosignal measuring apparatus may measure an electrical conductance of skin, hereinafter referred to as skin conductance, of the user. The skin conductance may be obtained based on a resistance or an impedance between two points of skin. A nervous system of a human being may be divided into a central nervous system and an automatic nervous system. The automatic nervous system may be activated irrespective of a human intention. When sympathetic nerves in the automatic nervous system are activated, perspiration may occur in a portion of a body. Sweat glands responsive to the sympathetic nerves may be distributed mainly in a forehead, a finger, a palm of a hand, and a sole of a foot. Thus, measuring a skin conductance of the finger, the palm, or the sole may facilitate an observation of a response of automatic nerves.

The biosignal measuring apparatus may include electrodes to be in contact with the skin of the user to measure such a skin conductance. When a direct current (DC) power supply is used, the biosignal measuring apparatus may measure a resistance among the electrodes. Alternatively, when an alternating current (AC) power supply is used, the biosignal measuring apparatus may measure an impedance among the electrodes.

At operation 120, the biosignal measuring apparatus verifies whether the measured biosignal is in a reference range. The reference range may vary depending on a user. For example, the reference range may extend from 100 kilo-ohms (ku) to 1 mega-ohm (Me). However, the reference range described in the foregoing is provided only as an illustrative example and thus, the reference range may not be limited thereto. The biosignal of the user may be measured in a range exceeding the reference range or less than the reference range.

At operation 130, when the measured biosignal is not in the reference range, the biosignal measuring apparatus generates a biosignal adjustment event. The biosignal adjustment event may be used to control the biosignal measuring apparatus to allow a physical stimulus to be applied to the user. The biosignal adjustment event may be a control signal used for the biosignal measuring apparatus to generate heat. Alternatively, the biosignal adjustment event may be a control signal used for the biosignal measuring apparatus to be closely attached to the user.

At operation 140, the biosignal measuring apparatus adjusts a setting of the biosignal measuring apparatus in response to the biosignal adjustment event.

At operation 140, when the biosignal is not in the reference range, the biosignal measuring apparatus controls a temperature of a contact area of the biosignal measuring apparatus. The contact area may refer to an area in which the biosignal measuring apparatus is in contact with the user.

For example, when a measured skin conductance is less than the reference range, the biosignal measuring apparatus may generate heat in the contact area. The biosignal measuring apparatus may adjust a heat generation setting. In addition, the biosignal measuring apparatus may increase the temperature of the contact area. The biosignal measuring apparatus may adjust a temperature setting. In response to the heat generated in the contact area, sweat may be generated on the skin of the user being in contact with the contact area. Accordingly, the skin conductance of the user may increase due to the production of sweat and thus, the skin conductance may be included in the reference range.

For another example, when a measured skin conductance is greater than the reference range, the biosignal measuring apparatus may cool the contact area. The biosignal measuring apparatus may decrease the temperature of the contact area. When the contact area is cooled, the skin of the user being in contact with the contact area may no longer produce sweat. Accordingly, the skin conductance of the user may decrease due to the lack of production of sweat and thus, the skin conductance may be included in the reference range.

At operation 140, when the biosignal is not in the reference range, the biosignal measuring apparatus may change a grip between the contact area of the biosignal measuring apparatus and the skin of the user.

For example, when a measured skin conductance is less than the reference range, the biosignal measuring apparatus may release a grip between the contact area and the skin of the user. The biosignal measuring apparatus may tighten the biosignal measuring apparatus to the user. For another example, when a measured skin conductance is greater than the reference range, the biosignal measuring apparatus may release a grip between the biosignal measuring apparatus and the skin of the user. The biosignal measuring apparatus may increase a distance between the contact area of the biosignal measuring apparatus and the skin of the user of the biosignal measuring apparatus by releasing a grip between the biosignal measuring apparatus and the user of the biosignal measuring apparatus. When the degree of contact is reduced, that is, when the grip is released, a space between the contact area and the skin of the user may be expanded. When the space is widened, more ventilation may occur and thus, the skin conductance of the user may decrease.

In an example, the biosignal measuring apparatus may include a cuff, and a grip between the biosignal measuring apparatus and the user using the cuff may be adjusted. For example, the biosignal measuring apparatus may tighten the biosignal measuring apparatus to the skin of the user by applying pressure to the cuff.

The biosignal measuring apparatus may simultaneously control the temperature of the contact area and the grip between the biosignal measuring apparatus and the skin of the user.

In addition to the temperature of the contact area, the biosignal measuring apparatus may also control a temperature of a measurement area in which the biosignal is measured. For example, the measurement area may be an electrode that measures the biosignal. In the biosignal measuring apparatus, the contact area and the measurement area may be divided. The contact area may refer to an area in which the biosignal measuring apparatus and the skin of the user are in contact. The measurement area may refer to an area in which the biosignal is measured using the electrode. A control applied to the contact area may affect the skin of the user in contact with the measurement area. When a direct control is applied to the measurement area, the biosignal measuring apparatus may effectively operate to allow the measured biosignal to be included in the reference range.

When the measured biosignal is less than the reference range, the biosignal measuring apparatus may generate heat in the measurement area. In addition, when the measured biosignal is less than the reference range, the biosignal measuring apparatus may tighten the biosignal measuring apparatus to the user. For example, the biosignal measuring apparatus may include the cuff, and thus tighten the biosignal measuring apparatus to the user using the cuff. The biosignal measuring apparatus may generate the heat or tighten the biosignal measuring apparatus to the user to allow the biosignal to be included in the reference range.

Conversely, when the measured biosignal is greater than the reference range, the biosignal measuring apparatus may cool the measurement area. In addition, when the measured biosignal is greater than the reference range, the biosignal measuring apparatus may release a grip between the biosignal measuring apparatus and the user. The biosignal measuring apparatus may cool the measurement area or release the grip to allow the biosignal to be included in the reference range.

In an example, when the setting of the biosignal measuring apparatus is adjusted, the biosignal measuring apparatus may verify whether the biosignal is in the reference range. The biosignal may be changed based on the adjusting of the setting of the biosignal measuring apparatus. The biosignal measuring apparatus may determine whether to terminate the adjusting of the setting. When the biosignal reaches the reference range, the biosignal measuring apparatus may terminate the adjusting of the setting. However, when the biosignal is still out of the reference range, the biosignal measuring apparatus may adjust the setting. The biosignal measuring apparatus may adjust the setting until the biosignal reaches the reference range.

Figure 2:
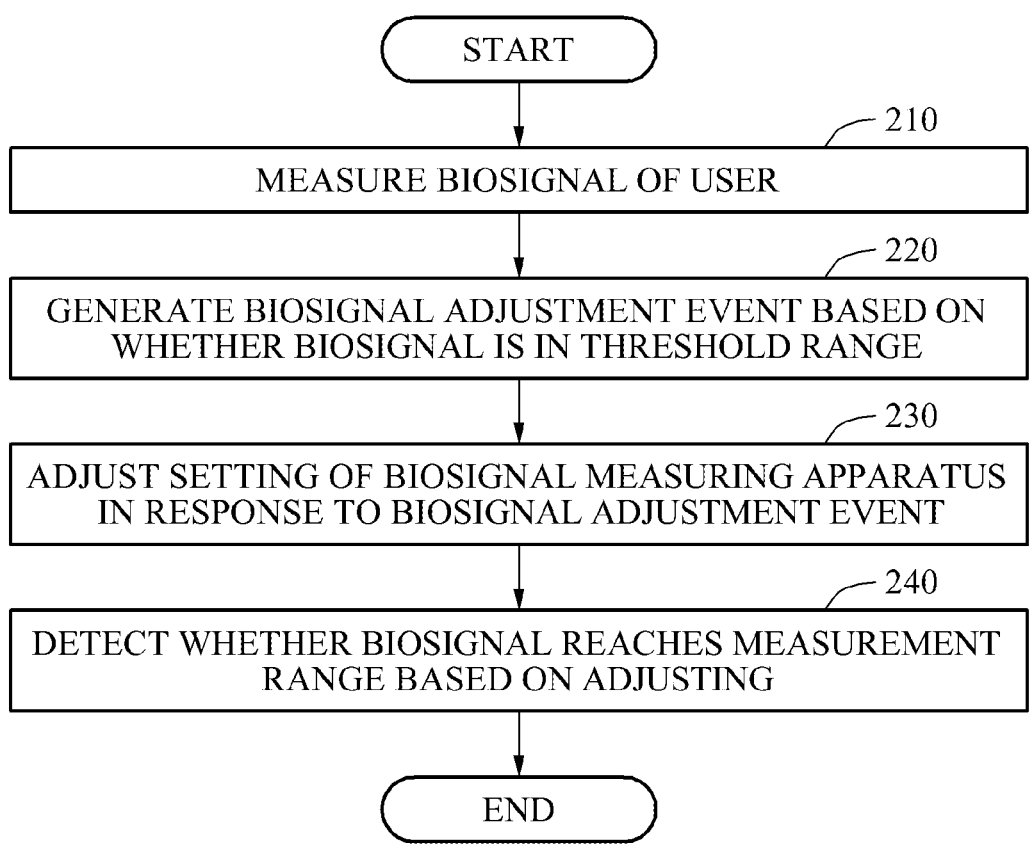
FIG. 2 is a flowchart illustrating another example of a biosignal measuring method.

FIG. 2 is a flowchart illustrating another example of a biosignal measuring method. The biosignal measuring method to be described hereinafter with reference to FIG. 2 may be performed by a biosignal measuring apparatus.

Referring to FIG. 2, at operation 210, the biosignal measuring apparatus measures a biosignal of a user. For example, the biosignal measuring apparatus may measure a skin conductance of the user using an electrode.

At operation 220, the biosignal measuring apparatus generates a biosignal adjustment event based on whether the biosignal is in a threshold range. The biosignal measuring apparatus may preset the threshold range and a measurement range. The threshold range may refer to a range associated with generation of the biosignal adjustment event. When the biosignal is out of the threshold range, the biosignal measuring apparatus may generate the biosignal adjustment event. The measurement range may refer to a measurable range of a biosignal. When the biosignal is out of the threshold range, the biosignal measuring apparatus may operate to allow the biosignal to be included in the measurement range.

At operation 230, the biosignal measuring apparatus adjusts a setting of the biosignal measuring apparatus in response to the biosignal adjustment event.

In an example, when the biosignal is less than a first boundary value of the threshold range, the biosignal measuring apparatus may adjust the setting to generate heat in a measurement area in which the biosignal is to be measured. When the threshold range includes "A" and "B," and the biosignal is less than A, the biosignal measuring apparatus may generate heat in the measurement area to allow the biosignal to be greater than or equal to A. Here, the threshold range may be from A to B. Alternatively, when the biosignal is less than the first boundary value of the threshold range, the biosignal measuring apparatus may adjust the setting to allow the tightening of the biosignal measuring apparatus to the user.

In another example, when the biosignal is greater than a second boundary value of the threshold range, the biosignal measuring apparatus may adjust the setting to allow the measurement area to be cooled. When the threshold range includes "A" and "B," and the biosignal is greater than B, the biosignal measuring apparatus may cool the measurement area to allow the biosignal to be less than or equal to B. Alternatively, when the biosignal is greater than the second boundary value, the biosignal measuring apparatus may adjust the setting to reduce a grip between the biosignal measuring apparatus and the user.

When the measured biosignal is out of the threshold range, the biosignal measuring apparatus may not readily observe a change in a biosignal responsive to sympathetic nerves. For example, the biosignal measuring apparatus may measure a skin conductance and a change in the skin conductance based on sweat produced by an activity of the sympathetic nerves. The skin conductance may be changed by the sweat produced by the activity of the sympathetic nerves. When skin of the user is wet before the sweat is produced by the activity of the sympathetic nerves, the change in the skin conductance may be small despite the production of the sweat by the activity of the sympathetic nerves. When the change in the skin conductance is small, detecting the change in the skin conductance may not be readily accomplished. In addition, when the skin of the user is dry, detecting the change in the skin conductance may not be easy despite the production of the sweat by the activity of the sympathetic nerves.

Thus, when the biosignal is maintained at a certain level, the biosignal measuring apparatus may sensitively detect a response of the sympathetic nerves.

At operation 240, the biosignal measuring apparatus detects whether the biosignal reaches the measurement range based on the adjusting of the setting. As described in the foregoing, the biosignal measuring apparatus may preset the measurement range. The measurement range may correspond to a measurable range of a biosignal. When the biosignal is in the measurement range, the biosignal measuring apparatus may detect a small change in the biosignal. The biosignal measuring apparatus may detect the response of the sympathetic nerves by allowing the biosignal to reach the measurement range. The biosignal in the measurement range may be valid data to be used as a subject of an analysis.

In an example, when a skin conductance of the user is less than the first boundary value of the threshold range, the biosignal measuring apparatus may generate heat to increase the biosignal. Alternatively, the biosignal measuring apparatus may increase a grip to the user. The biosignal measuring apparatus may detect whether the biosignal is greater than a first boundary value of the measurement range based on an operation of generating the heat or an operation of closely attaching the biosignal measuring apparatus to the user. When the measurement range includes "a" and "b," the biosignal measuring apparatus may detect whether the biosignal is greater than "a" based on the operations. The biosignal measuring apparatus may continuously perform the operation of generating the heat or the operation of closely attaching the biosignal measuring apparatus to the user until the biosignal exceeds "a." Thus, the biosignal measuring apparatus may continuously generate an amount of heat until the biosignal exceeds "a."

Here, the first boundary value of the measurement range may be equal to the first boundary value of the threshold range. Alternatively, the first boundary value of the measurement range may be greater than the first boundary value of the threshold range. When the biosignal exceeds the first boundary value of the measurement range, the biosignal measuring apparatus may terminate the operation of generating the heat or the operation of tightening the biosignal measuring apparatus to the user.

In another example, when a skin conductance of the user is greater than the second boundary value of the threshold range, the biosignal measuring apparatus may cool the biosignal measuring apparatus to decrease the biosignal or release a grip between the biosignal measuring apparatus and the user. The biosignal measuring apparatus may detect whether the biosignal is less than or equal to a second boundary value of the measurement range based on an operation of cooling or an operation of releasing the grip between the biosignal measuring apparatus and the user. When the measurement range includes "a" and "b," the biosignal measuring apparatus may detect whether the biosignal is less than or equal to "b" based on the operations. The biosignal measuring apparatus may continuously perform the operation of cooling or the operation of releasing the grip until the biosignal becomes less than or equal to "b." Thus, the biosignal measuring apparatus may loosen the grip between the biosignal measuring apparatus and the user until the biosignal becomes less than or equal to "b."

Here, the second boundary value of the measurement range may be equal to the second boundary value of the threshold range. Alternatively, the second boundary value of the measurement range may be less than the second boundary value of the threshold range. When the biosignal is less than the second boundary value of the measurement range, the biosignal measuring apparatus may terminate the cooling operation or the operation of releasing the grip between the measuring apparatus and the user of the apparatus.

Figure 3:
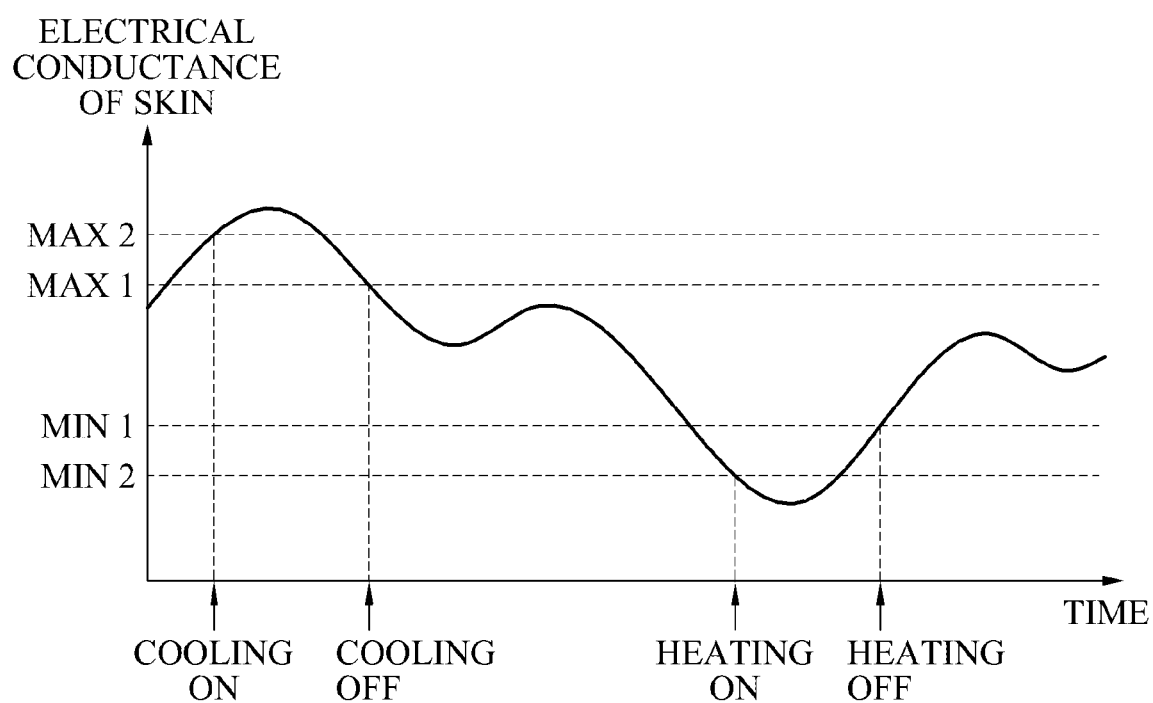
FIG. 3 is a graph illustrating an example of a change in a biosignal.

FIG. 3 is a graph illustrating an example of a change in a biosignal.

FIG. 3 illustrates an example of a change in a skin conductance of a user. The skin conductance illustrated in FIG. 3 may be used only as an illustrative example and thus, a biosignal may not be limited to the skin conductance.

Referring to FIG. 3, the threshold range described with reference to FIG. 2 includes from "MIN 2" to "MAX 2." Also, the measurement range described with reference to FIG. 2 includes from "MIN 1" to "MAX 1." For ease of description, the threshold range and the measurement range are distinguishably illustrated in FIG. 3. In an example, the threshold range and the measurement range may be equal to each other. In addition, MIN 2 of the threshold range may be equal to MIN 1 of the measurement range, and MAX 2 of the threshold range may be equal to MAX 1 of the measurement range.

Referring to FIG. 3, at an initial stage, the skin conductance of the user continuously increases to exceed MAX 2. When the skin conductance exceeds MAX 2, a biosignal measuring apparatus may perform a "cooling on" operation. For example, the cooling on operation may include cooling the biosignal measuring apparatus. In addition, the cooling on operation may include releasing a grip between the biosignal measuring apparatus and the user of the apparatus for ventilation and generating wind. When the skin conductance exceeds MAX 2, which is a first boundary value of the threshold range, the biosignal measuring apparatus may perform an operation to decrease the skin conductance.

As time elapses, the skin conductance may decrease by the cooling on operation. The biosignal measuring apparatus may monitor the skin conductance. When the skin conductance becomes less than or equal to MAX 1, the biosignal measuring apparatus may terminate the cooling operation, which corresponds to a "cooling off" operation.

As illustrated in FIG. 3, the skin conductance may then be in the measurement range. The skin conductance may be maintained at a certain level within the measurement range. The skin conductance may sensitively detect a response of sympathetic nerves. The biosignal measuring apparatus may accurately detect a change in the skin conductance based on an activity of the sympathetic nerves.

For example, skin of the user may be dry, and the skin conductance of the user may be in a range less than the threshold range. The biosignal measuring apparatus may detect whether the skin conductance is less than MIN 2. When the skin conductance is less than MIN 2, the biosignal measuring apparatus may perform a "heating on" operation. For example, the heating on operation may include generating heat by the biosignal measuring apparatus. The biosignal measuring apparatus may increase a temperature of an electrode and generate the heat. In addition, the heating on operation may include tightening the biosignal measuring apparatus to the user. When the skin conductance is less than MIN 2, which is a second boundary value of the threshold range, the biosignal measuring apparatus may perform on operation to increase the skin conductance.

As time elapses, the skin conductance may increase by the heating on operation. The biosignal measuring apparatus may monitor the skin conductance. When the skin conductance becomes less than and equal to MIN 1, the biosignal measuring apparatus may terminate the heating on operation, which corresponds to a "heating off" operation.

Figure 4:
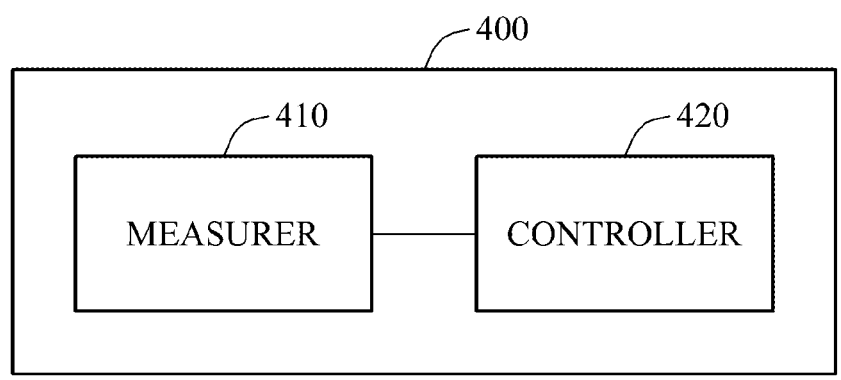
FIG. 4 is a diagram illustrating an example of a biosignal measuring apparatus.

FIG. 4 is a diagram illustrating an example of a biosignal measuring apparatus.

Referring to FIG. 4, the biosignal measuring apparatus 400 includes a measurer 410 and a controller 420.

The measurer 410 measures a biosignal of a user of the measuring apparatus 400. For example, the measurer 410 may measure a skin conductance of the user of the measuring apparatus 400. The measurer 410 includes an electrode to be in contact with the skin of the user of the measuring apparatus 400. The measurer 410 electrically connects the biosignal measuring apparatus 400 to the user. Due to the electrical connection, a closed loop may be formed between the biosignal measuring apparatus 400 and the user. The skin conductance to be measured by the measurer 410 is provided only as an illustrative example and thus, the biosignal to be measured by the measurer 410 may not be limited to the skin conductance.

The controller 420 verifies whether the measured biosignal is in a reference range. When the measured biosignal is not in the reference range, the controller 420 generates a biosignal adjustment event. The biosignal adjustment event may be used to control the biosignal measuring apparatus 400 to allow a physical stimulus to be applied to the user. The biosignal adjustment event may be a control signal to allow the biosignal measuring apparatus 400 to generate heat. Alternatively, the biosignal adjustment event may be a signal to control the biosignal measuring apparatus 400 to tighten around the user of the biosignal measuring apparatus 400.

The controller 420 adjusts a setting of the biosignal measuring apparatus 400 in response to the biosignal adjustment event. For example, when the biosignal is not in the reference range, the controller 420 may control a temperature of a contact area between the biosignal measuring apparatus 400 and the user of the measuring apparatus 400. When the biosignal is in a range less than the reference range, the controller 420 may adjust a temperature setting of the contact area so as to increase the temperature of the contact area between the measuring apparatus 400 and the user of the measuring apparatus 400. The controller 420 may generate a control command to allow the contact area to generate heat. In addition, the controller 420 may control a change in a grip between the biosignal measuring apparatus 400 and the user of the biosignal measuring apparatus 400. When the biosignal is not in the reference range, the controller 420 may control the biosignal measuring apparatus 400 to tighten around the user of the biosignal measuring apparatus 400.

In an example, when the biosignal is in the range less than the reference range, the controller 420 may control the measurer 410. When the biosignal is in the range less than the reference range, the controller 420 may control the measurer 410 to generate heat in the measurer 410. In addition, when the biosignal is in the range less than the reference range, the controller 420 may control the biosignal measuring apparatus 400 to tighten around the user of the measuring apparatus 400. When heat is generated in an area in which the biosignal is to be measured or in an area in which the biosignal measuring apparatus 400 is in contact with the user of the measuring apparatus 400, the skin of the user of the measuring apparatus 400 may produce sweat. Thus, the skin conductance may increase due to the production of sweat.

In another example, when the biosignal is in a range greater than the reference range, the controller 420 may control the measurer 410. When the biosignal is in the range greater than the reference range, the controller 420 may cool the measurer 410. In addition, when the biosignal is in the range greater than the reference range, the controller 420 may control a grip between the biosignal measuring apparatus 400 and the user to be reduced. The controller 420 may control the biosignal measuring apparatus 400 to perform an operation of releasing the grip between the biosignal measuring apparatus 400 and the user of the measuring apparatus 400. When the grip is released, a space between the biosignal measuring apparatus 400 and the skin of the user may be expanded. When the space is expanded, air may circulate between the measuring apparatus 400 and the user of the measuring apparatus 400 and wet skin may be dried thus decreasing skin conductance.

The controller 420 verifies whether the biosignal is in the reference range based on the adjusting of the setting of the biosignal measuring apparatus 400. The controller 420 adjusts the setting of the measuring apparatus 400 until the biosignal reaches the reference range. When the biosignal reaches the reference range, the controller 420 may terminate the adjusting of the setting.

Descriptions provided with reference to FIGS. 1 through 3 may be applicable hereto and thus, repeated description will be omitted here for brevity.

Figure 5:
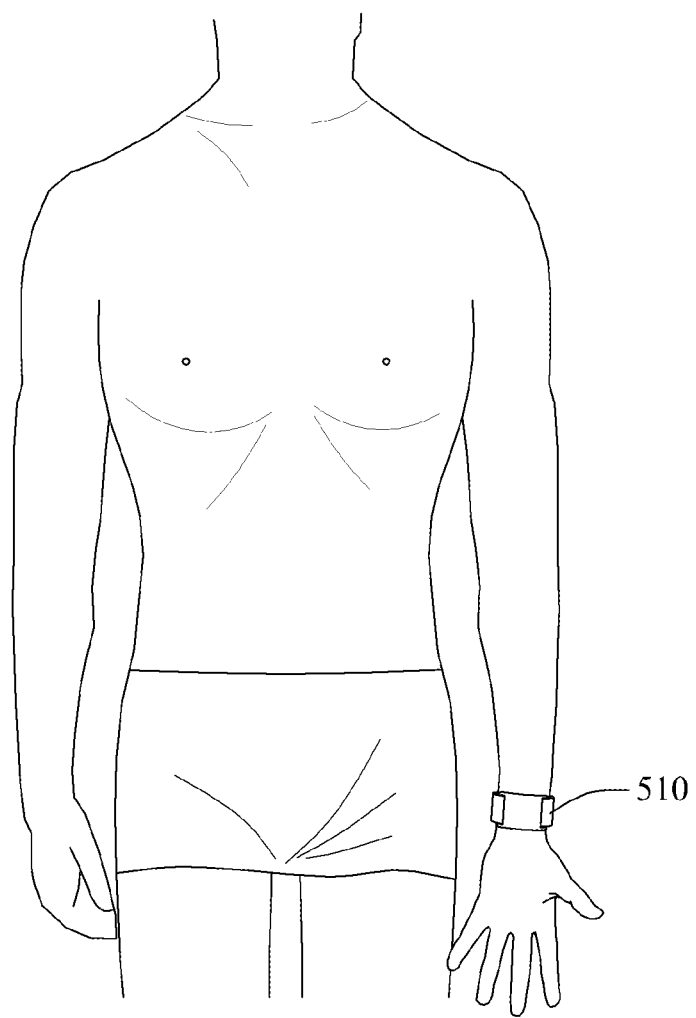
FIG. 5 is a diagram illustrating an example of a wearable biosignal measuring apparatus.

FIG. 5 is a diagram illustrating an example of a wearable biosignal measuring apparatus.

Referring to FIG. 5, a user wears a wearable device 510. The wearable device 510 may measure a biosignal of the user. For example, the wearable device 510 may measure skin conductance, a degree of skin hydration, or a degree of skin dryness. In addition, the wearable device 510 may measure blood pressure of the user.

The wearable device 510 may include a transmitter. The wearable device 510 may transmit the measured biosignal to a user terminal through the transmitter. For example, the device 510 may transmit the biosignal through a Bluetooth device or a near field communication (NFC) module. The wearable device 510 may encode the measured biosignal and transmit the encoded biosignal to the user terminal. The wearable device 510 may form a wireless body area network (WBAN) in conjunction with the user terminal.

The wearable device 510 may include a display (not shown). The wearable device 510 may output the measured biosignal to the display. The user may then verify the biosignal output on the display. For example, when a measured skin conductance is less than a predetermined value, the wearable device 510 may generate heat in an area in which the wearable device 510 is in contact with the skin of the user or in an electrode of the wearable device 510. The skin of the user may then produce sweat in response to the generation of the heat and thus, the skin conductance may increase due to the production of the sweat. The user may verify a change in the skin conductance output on the display.

Figure 6A:
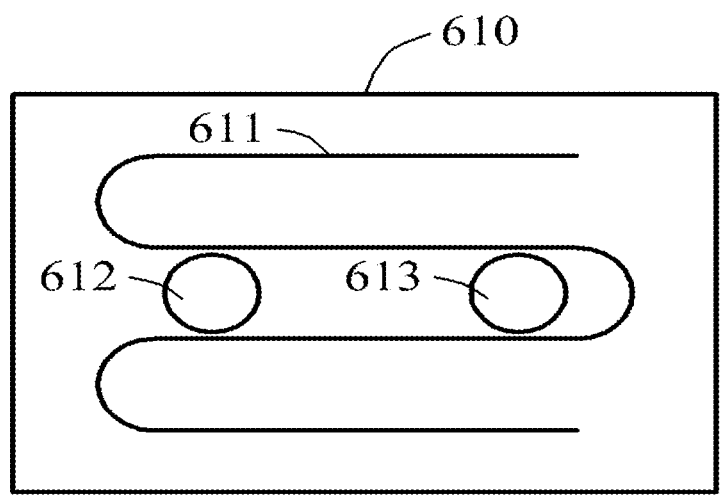
FIGS. 6A and 6B are diagrams illustrating examples of a contact area of a biosignal measuring apparatus.
Figure 6B:
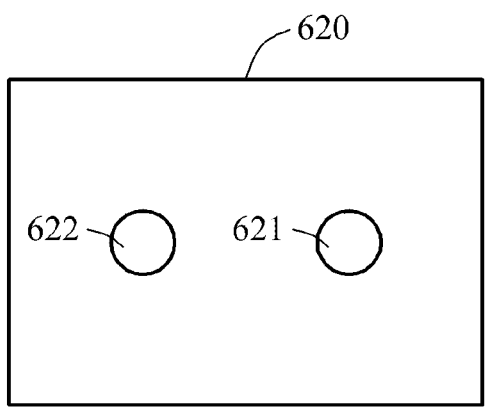

FIGS. 6A and 6B are diagrams illustrating examples of a contact area of a biosignal measuring apparatus.

Referring to FIG. 6A, a contact area 610 includes a hot wire 611 and electrodes, for example, 612 and 613. The contact area 610 may be an area in which the biosignal measuring apparatus is in contact with the skin of a user of the biosignal measuring apparatus. The electrodes 612 and 613 may measure a biosignal of the user. For example, the electrodes 612 and 613 may measure a skin conductance of the user. The electrodes 612 and 613 may be a measurement area in which the biosignal of the user is to be measured.

The contact area 610 may generate heat through the hot wire 611. The skin of the user in contact with the contact area 610 may produce sweat in response to the heat generated by the hot wire 611. Thus, the skin conductance of the user of the biosignal measuring apparatus may increase due to the production of sweat.

Referring to FIG. 6B, a contact area 620 includes electrodes, for example, 621 and 622. Although not illustrated in FIG. 6B, the electrodes 621 and 622 may include a hot wire. The electrodes 621 and 622 may generate heat through the hot wire. In a case of the contact area 610, illustrated in FIG. 6A, the heat may be generated in all areas. However, in a case of the contact area 620, illustrated in FIG. 6B, the heat may be generated in a measurement area in which the biosignal of the user is to be measured.

Although a contact area and a measurement area are distinguishably illustrated in FIGS. 6A and 6B, the contact area and the measurement area may be identical.

Figure 7:
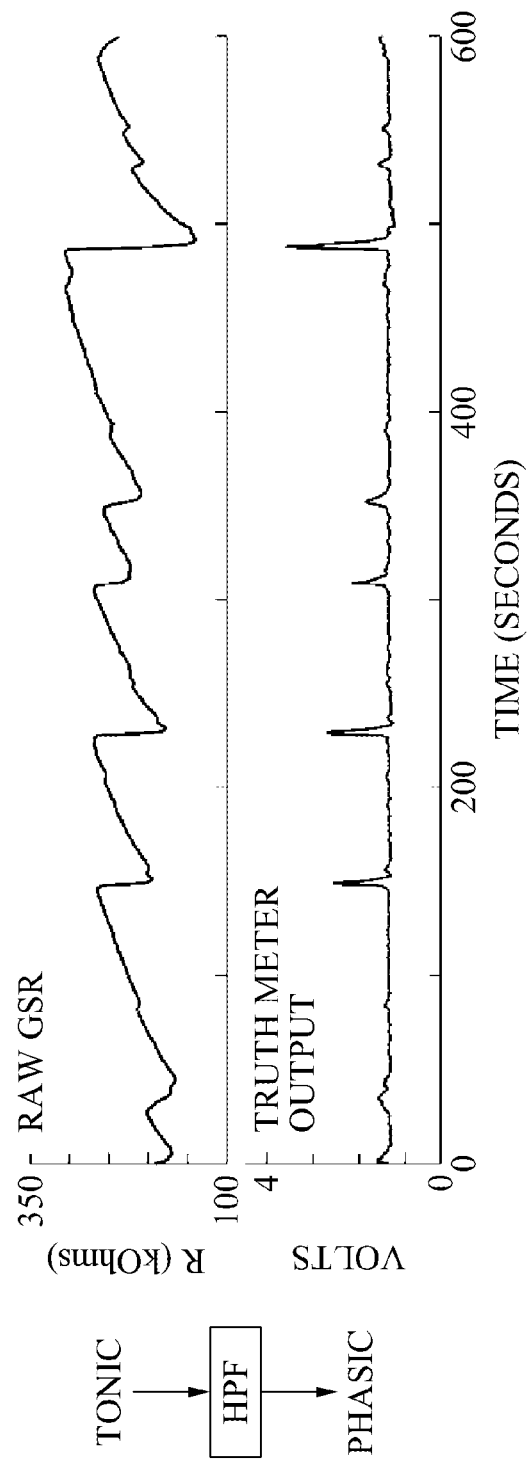
FIG. 7 is a diagram illustrating an example of a signal measured by a biosignal measuring apparatus.

FIG. 7 is a diagram illustrating an example of a signal measured by a biosignal measuring apparatus.

Referring to FIG. 7, a raw signal measured by the biosignal measuring apparatus is also referred to as a "tonic." A skin conductance illustrated in a first graph indicates the tonic. A y axis of the first graph indicates a resistance, which is an inverse of a galvanic skin response (GSR). At a point, sweat may be produced by a response of sympathetic nerves. Referring to the first graph, the resistance decreases at each point in time at which the sweat is produced.

When the biosignal measuring apparatus filters the tonic using a high-pass filter (HPF), the biosignal measuring apparatus may extract a "phasic" from the tonic. The tonic may be a low-frequency component of a skin conductance, and the phasic may be a high-frequency component of the skin conductance. The biosignal measuring apparatus may extract a point in time at which the skin conductance is suddenly changed based on the phasic.

In an example, when the tonic deviates from a predetermined range, the biosignal measuring apparatus may perform a predetermined operation to allow the tonic to enter the predetermined range. To analyze a small change in the tonic in the predetermined range, the biosignal measuring apparatus may filter the tonic. The biosignal measuring apparatus may obtain the phasic from the tonic as a result of the filtering. The biosignal measuring apparatus may then verify the point in time at which the skin conductance is suddenly changed based on the phasic.

The units described herein may be implemented using hardware components and software components. For example, the hardware components may include microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums. The non-transitory computer readable recording medium may include any data storage device that can store data which can be thereafter read by a computer system or processing device. Examples of the non-transitory computer readable recording medium include read-only memory (ROM), random-access memory (RAM), CD-ROMs, magnetic tapes, floppy disks, optical data storage devices, etc. Also, functional programs, codes, and code segments that accomplish the examples disclosed herein can be easily construed by programmers skilled in the art to which the examples pertain based on and using the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A biosignal measuring apparatus, comprising:
a processor configured to
measure a biosignal of a user of the biosignal measuring apparatus,
verify whether the biosignal is in a reference range, and
control at least one of a temperature of a contact are between the user and the biosignal measuring apparatus or a change in grip between the user and the biosignal measuring apparatus based on whether the biosignal deviates from the reference range.

2. The apparatus of claim 1, wherein the contact area comprises hot wires and electrodes.

3. The apparatus of claim 2, wherein the hot wires generate heat and the electrodes measure the biosignal of the user of the apparatus.

4. The apparatus of claim 1, wherein, in response to the biosignal being in a range less than the reference range, the processor is further configured to perform at least one of an operation of generating heat in a measurement area in which the biosignal is measured or an operation of tightening the biosignal measuring apparatus to the user.

5. The apparatus of claim 1, wherein, in response to the biosignal being in a range greater than the reference range, the processor is further configured to perform at least one of an operation of cooling a measurement area in which the biosignal is measured or an operation of releasing a grip between the biosignal measuring apparatus and the user.

6. The apparatus of claim 1, wherein the processor is further configured to verify whether the biosignal is in the reference range based on the adjusting of the setting, and to terminate the adjusting of the setting based on a result of the verifying.

7. The apparatus of claim 1, further comprising a transmitter configured to transmit the measured biosignal to a user terminal.

* * * * *